United States Patent [19]

Chen

[11] Patent Number: 5,472,708
[45] Date of Patent: Dec. 5, 1995

[54] PULSATILE PARTICLES DRUG DELIVERY SYSTEM

[75] Inventor: Chih-Ming Chen, Cooper City, Fla.

[73] Assignee: Andrx Pharmaceuticals Inc., Fort Lauderdale, Fla.

[21] Appl. No.: 290,815

[22] PCT Filed: Nov. 2, 1993

[86] PCT No.: PCT/US93/10643

§ 371 Date: Aug. 16, 1994

§ 102(e) Date: Aug. 16, 1994

[87] PCT Pub. No.: WO94/12160

PCT Pub. Date: Jun. 9, 1994

Related U.S. Application Data

[63] Continuation-in-part of Ser. No. 982,761, Nov. 27, 1992, Pat. No. 5,260,069.

[51] Int. Cl.$^6$ ..................... A61K 9/48
[52] U.S. Cl. ............ 424/451; 424/458; 424/464; 424/462; 424/474
[58] Field of Search .................. 424/451, 438, 424/468, 472

[56] References Cited

U.S. PATENT DOCUMENTS

| | | | |
|---|---|---|---|
| 4,716,041 | 12/1987 | Kjornaes et al. | 424/468 |
| 5,017,381 | 5/1991 | Maruyama et al. | 424/472 |
| 5,110,597 | 5/1992 | Wong et al. | 424/438 |
| 5,213,808 | 5/1993 | Bar-Shalom et al. | 424/473 |

Primary Examiner—Thurman K. Page
Assistant Examiner—William E. Benston, Jr.
Attorney, Agent, or Firm—Alvin S. Blum

[57] ABSTRACT

Unit dosage form for delivering drugs into the body in a series of sequential, pulsatile releasing events employs conventional pharmaceutical equipment and processes for optimum economy, reliability, and bioavailability. The system can be used with drugs which cannot be released by diffusion through a porous coating, such as water insoluble drugs. A plurality of populations of pellets is provided within a unit dosage form such as a capsule (8) or tablet. The pellets are composed of a core containing the drug (3) and a swelling agent (4) which expands in volume when exposed to water. The core is enclosed within a membrane or coating which is permeable to water. The membrane is composed of a water insoluble and permeable film forming polymer, a water soluble film forming polymer (11) and a permeability reducing agent (14). When the unit dose releases the pellets into the digestive tract, water diffuses through the coating and into the core. As water is taken up by the swelling agent, the core expands, exerting force on the coating until it bursts, releasing the drug. The permeability reducing agent reduces the rate at which water reaches the swelling agent, thereby delaying release time. The water soluble polymer dissolves, weakening the coating so that it bursts sooner. By varying the proportions of the three coating ingredients and/or coating thickness from one pellet population to another, the release timing of the pellets can be very effectively controlled.

16 Claims, 1 Drawing Sheet

5,472,708

PULSATILE PARTICLES DRUG DELIVERY SYSTEM

This is a continuation in part of U.S. patent application Ser. No. 07/982,761 filed Nov. 27, 1992 issued Nov. 9, 1993 as U.S. Pat. No. 5,260,069 and PCT application Ser. No. PCT/US93/10643 filed Nov. 2, 1993.

TECHNICAL FIELD

My invention relates to controlled absorbtion drug delivery systems and more particularly to combined coating dissolution and explosion mechanisms in coated drug-containing pellets for assured timely release of orally administered pharmaceuticals.

BACKGROUND ART

A unique sustained-release drug delivery system, Time-Controlled Explosion System (TCES), was described in U.S. Pat. No. 4,871,549 issued Nov. 3, 1989 to Ueda et al. Drug release is caused by explosion of an insoluble, water permeable membrane after a definite period of time. Beads or granules contain the drug and a swelling agent enclosed by the water insoluble membrane. Water permeates the membrane and causes the swelling agent to expand until the internal forces on the membrane cause it to burst or explode, thereby releasing the drug. This mechanism is especially useful with water insoluble drugs in which those prior art delay mechanisms related to diffusion of the drug through a permeable coating would not be effective.

A remarkable feature of the TCES is that drug is not released from the completely coated pellets or spheres until the membrane bursts, and then it is all available. This can provide for a pulse of drug release. The lag time before release is related to the thickness of the membrane with maximum lag times of approximately four hours reported by Ueda.

One of the principal uses for delayed release forms of medication is to provide for a once a day oral administration that releases drug in a continuous controlled rate or in a series of sequential pulses throughout the 24 hour period. This ensures a reasonably uniform blood level for maximum efficacy with the least toxic effect from high peaks of blood concentration. This is not easily accomplished with the system of Ueda because the insoluble membrane must be made very thick for long delays, and this makes explosion less reliable. If the membrane never bursts, the drug will be lost in the stool and the patient will get less drug than prescribed and never be aware of it. Furthermore, in cases where there is a delayed stomach emptying time, much of the explosion may take place in the stomach and not be available for absorbtion until the pyloric sphincter opens. This may present a very large dose for sudden absorbtion that may be very dangerous. Furthermore, acid unstable drugs should not be released to the acidic stomach contents, where an indeterminate portion of the drug dose may be destroyed.

DISCLOSURE OF THE INVENTION

It is accordingly an object of the invention to provide unit dosage forms for drugs or therapeutic agents that will release the drug into the environment of use in a series of sequential, pulsatile releasing events that employs conventional pharmaceutical equipment and products such as roller compaction methods for optimum economy, reliability and bioavailability. It is another object to provide dosage units readily adaptable to a variety of timing intervals, different therapeutic agents and combinations of agents, including agents which cannot be released by diffusion through an insoluble coating. It is yet another object to provide a system that can yield a large number of pulses within a single unit dosage form at no significant increase in cost over only one or two pulses. It is yet another object of the invention to provide means for protecting the drug from adverse environmental conditions prior to delivery into the environment of use. It is yet another object of the invention to provide a drug delivery system in which the explosive pellets mechanism for drug release is modified by changing the coating to delay the explosion event in a more controllable and reliable fashion than simply increasing the thickness of the insoluble coating.

The coating of the invention is provided with two means to alter release time of the drug. A first means for altering of the invention comprises the incorporation of a water soluble polymer along with the insoluble, water permeable coating material of the prior art. This water soluble polymer is of the enteric coating polymer type in which the polymer becomes soluble only at pH values above certain specific values. This prevents dissolving of the polymer in the stomach. When the pellet reaches the elevated pH of the intestine, the polymer begins to dissolve and weaken the membrane coating, so that explosion of the weakened membrane can be assured after a predetermined time of exposure to the intestinal environment. By varying the proportion of soluble and insoluble material in the coating as well as the coating thickness, the time delay before explosion can be prolonged with better control and reliability, with eventual disintegration of the coating ensuring release of the drug.

A second means for altering release of the drug comprises the incorporation into the coating of material which reduces the permeability of the coating. By reducing the rate of influx of water into the interior of the pellet containing the swelling agent, the rate of swelling can be reduced and the time to explosion can be prolonged and controlled. Either of these means of modifying the coating may be used separately or in combination.

These and other objects, advantages and features of the invention will become more apparent when the detailed description is studied in conjunction with the drawings.

BEST MODE FOR CARRYING OUT THE INVENTION

Figure 1:
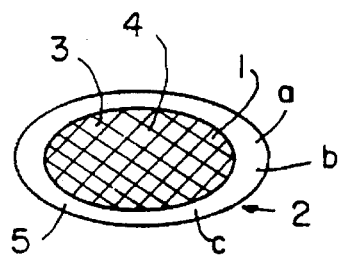
FIG. 1 shows diagrammatically a pellet of the invention with a core prepared by roller compaction with a mixture of swelling agent and active drug.

Referring now first to FIG. 1, an individual pellet 2 of the invention comprises a core 1 prepared by the well known, economical, roller compaction method with sieving to select granules of particular mesh size and irregular configuration containing a combination of active drug 3 and swelling agent 4. The coating membrane 5 completely encloses the core 1. The coating membrane contains:

a) a water insoluble, water permeable polymer;

b) an enteric coating polymer (a polymer soluble in water at PH values above a certain value;

c) a diffusion controlling agent which reduces the permeability of the coating to water.

Figure 2:
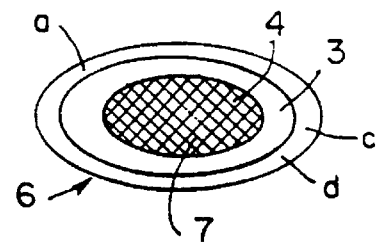
FIG. 2 shows diagrammatically a pellet of the invention with a core of a sugar seed coated with a mixture of swelling agent and active drug.

Referring now to FIG. 2, an individual pellet 6 of the invention comprises a bead core 7 of sugar. This is coated with a layer of a mixture of active drug 3 and swelling agent 4 by spray coating in a fluidized bed as is well known in the art. The layer of active drug and swelling agent is then enclosed by an outer coating membrane 5. The coating membrane contains:

a) a water insoluble, water permeable polymer; and one or both of:

c) a diffusion controlling agent d) a dissolution controlling agent

The preparation and coating of the pellets may be performed by any of the processes well known in the art, and the order in which the various ingredients are laid down may be varied as desired, with drug and swelling agent inside the frangible coating. The frangible coating may be constructed to increase or decrease the lag time to release by varying the proportions of insoluble polymer, soluble polymer and diffusion controlling agent. The thickness of The outer coating and the amount of swelling agent may also be adjusted. When control must be exerted over where in the digestive tract release is to occur, the dissolution agent may be of the enteric type wherein solubility increases at higher pH.

The system may be used with water soluble as well as water insoluble drugs or combinations of drugs.

Water permeable and insoluble film-forming polymer materials for the coating may include cellulose derivatives, acrylic resins, copolymers of acrylic acid and methacrylic acid esters with quaternary ammonium groups and copolymers of acrylic acid and methacrylic acid esters. Permeation retarding materials may include ingredients such as the fatty acids, waxes, and the salts of the fatty acids such as magnesium stearate and calcium stearate. The pharmaceutical grades may not be pure stearates, but may contain small mounts of other fatty acid salts.

Swelling agent s may include:

cross-linked polyvinyl pyrrolidone cross-linked carboxymethylcellulose;

sodium starch glycolate and pregelatinized starch.

Water permeable and soluble film forming agents may include the enteric polymers which have greatly increased solubility at alkaline pH such as: cellulose acetate phthalate; cellulose acetate trimellitate; shellec; methacrylic acid copolymers, USP/NF, such as the Eudraget formulations of Rohm Pharma GNBH of Weiterstadt; and hydroxypropyl methylcellulose phthalate.

Water permeable and slowly soluble film forming agents whose solubility is substantially independent of pH include hydroxypropyl methylcellulose and polyvinyl pyrrolidone.

The following examples describe typical formulations of multiparticulate, pulsatile unit dosage forms and methods of manufacture thereof:

EXAMPLE 1

| | |
|---|---|
| Nifedipine, a drug | 200 g |
| Explotab, a swelling agent, a starch glycolate | 200 g |
| Povidone K90, a binding agent, polyvinyl pyrrolidone | 20 g |
| Ethanol | 1800 g |

The above three raw materials were first dispersed in the ethanol until uniform. The suspension was then spray coated onto 400 g of sugar spheres (size 40 to 50 mesh) in a fluidized bed coater equipped with a Wurster column. Six hundred grams of the Nifedipine pellets are then coated with the following polymer suspension:

| | |
|---|---|
| Ethylcellulose, an insoluble polymer | 90 g |
| Eudragit S100, an ethacrylic acid copolymer slowly soluble in intestinal fluid | 45 g |
| Magnesium Stearate, a hydrophobic agent reducing permeability | 15 g |
| Ethanol | 1800 g |

At the time intervals when about 25%, 50% and 75% of the coatings suspension are consumed, the coating machine is stopped and 50 grams of samples are collected. Then coating continues until all of the coating material is consumed. These four simples coated with different amounts of polymer will give various lag times when placed in an aqueous medium. Forty grams of the above four types (i.e. coated with four different levels of polymer) of coated pellets are then mixed with 25 grams of microcrystalline cellulose, 13 grams of Polyplasdone XL, a cross-linked PVP disintegrant from GAF Chemical Corp., and 2 grams of Myvatex, a lubricant for compression. The above mixture is then compressed into suitable size of tablets. This tablet will give a pulsatile pellet delivery system with four different releasing lag times. The four types of coated pellets can also be blended and encapsulated in a capsule dosage form.

EXAMPLE 2

| | |
|---|---|
| Zidovudine, a drug | 200 g |
| Explotab | 200 g |
| Povidone K O | 20 g |
| Ethanol | 1800 g |

The above three raw materials were first dispersed in the ethanol until uniform. The suspension was then spray coated onto 400 g of sugar spheres (size 40 to 50 mesh) in a fluidized bed coater equipped with a Wurster column. Six hundred grams of the zifedipine pellets are then coated with the following polymer suspension:

| | |
|---|---|
| Ethylcellulose | 90 g |
| HPMCP 55, enteric polymer, hydroxypropropyl methylcellulose phthalate, Eastman | 45 g |
| Magnesium Stearate | 15 g |
| Ethanol | 1800 g |

At the time intervale when about 50% of the coatings suspension are consumed, the coating machine is stopped and 50 grams of samples are collected. Then coating is resumed until all of the coating material is consumed. These two samples coated with different amounts of polymer will give different lag times when placed in an aqueous medium.

Forty five grams of the above two types (i.e. coated with two different levels of polymer) of coated pellets are then mixed with 45 grams of uncoated active pellets (for immediate release purpose), 7 grams of microcrystalline cellulose, 6 grams of Polyplasdone XL and 2 grams of Myvatex. The above mixture is then compressed into suitable size of tablets. This tablet will give a pulsatile pellet delivery system with three different releasing lag times.

The combination of a water soluble film forming agent with a permeability reducing agent in the coating with the insoluble film forming agent gives greater control over the frangibility of the coating and the rate of swelling.

Fluidized bed coaters are well known in the art and have been found useful in this process but other coating apparatus and methods well known in the art may be used with the invention as well.

The term "drug" as used herein includes, without limitation, antibiotics, tranquilizers, agents acting on the heart, liver, kidney, central nervous system and muscles, contraceptives, hormonal agents, antineoplastic agents useful in humans or animals and may include combinations of drugs.

The term "unit dosage form" includes, without limitation, discrete aggregates of populations of pellets contained in capsules, or compressed into tablets or suppositories with binding agent. The dosage form may be arranged to dissolve promptly in any aqueous medium or to resist dissolution in certain environments such as enteric coated tablets which will not release pellets until they have passed the acid stomach and reached the alkaline intestine.

Figure 3:
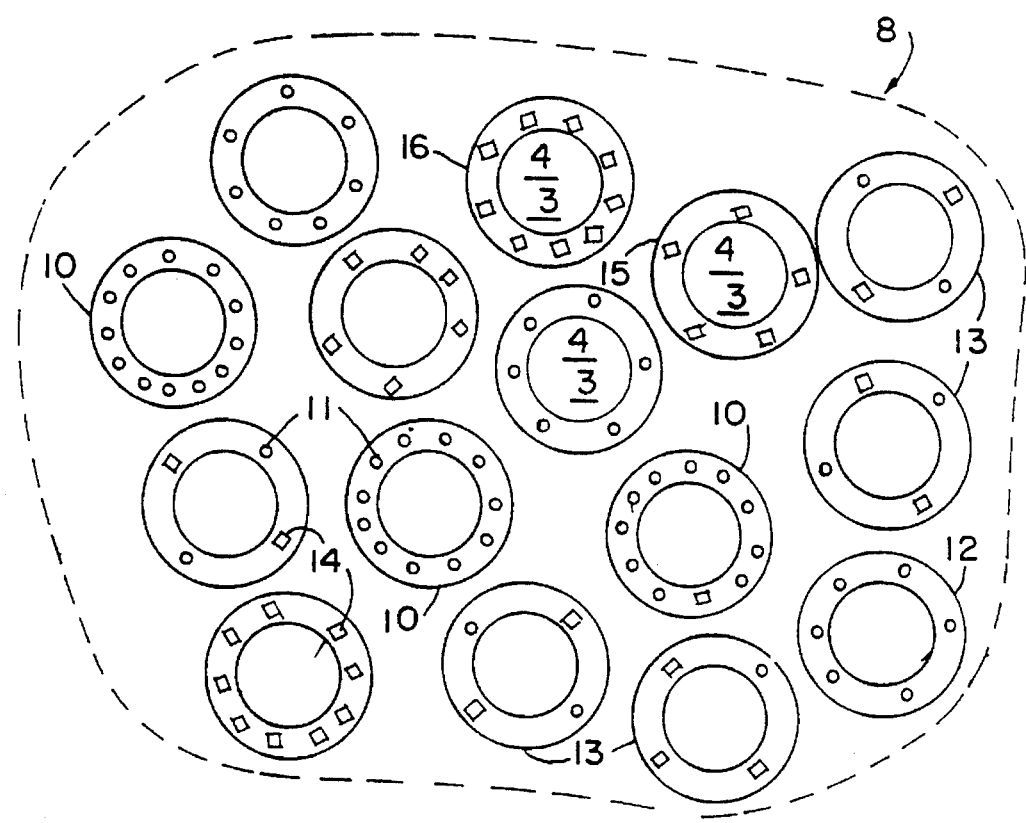
FIG. 3 shows diagrammatically a unit dose of the invention with pellets having five different release times.

Referring now to FIG. 3, a typical unit dosage form is shown diagrammatically as a carrier medium such as a tablet or a capsule 8 holding five populations of pellets. All of the pellets have identical cores containing swelling agent 4 and drug 3. All of the pellets have a coating that includes a water permeable and insoluble film forming agent. The coatings of the different populations are provided with other ingredients as well, to alter the time interval between initial exposure to water and final bursting of the pellet from imbibition of water and swelling.

The first-to-burst population of pellets 10 are provided with a high concentration of water soluble film forming agent indicated by circles 11. As the agent 11 is rapidly removed from the coating, the coating becomes more frangible, and is burst by a lower internal pressure from the swelling agent. The second-to-burst population of pellets 12 have a lower concentration of soluble film forming agent 11 which extends the time before the coating becomes so weak from loss of the agent that it bursts. The third-to-burst population of pellets 13 has, in addition to the water soluble film forming agent 11, some hydrophobic or permeability reducing agent 14 in the coating to slow down the rate at which water enters the core to swell the swelling agent 4. This increases the time lag before the pellets burst, releasing their contents. A fourth-to-burst population of pellets 15 has a coating with only permeability reducing agent 14 added in small concentration to reduce the rate of swelling. The fifth-to-burst population of pellets 16 is provided with a higher concentration of hydrophobic agent 14 to further reduce the rate of swelling to prolong further the lag time before release of the drug for the absorbtion.

The particles or pellets of the invention may include without limitation spheres, irregular shapes or large tablet shapes such as the well known "minitablets", for example, and their sizes may vary between 4 mm. down to about 0.1 mm.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

I claim:

1. A unit dosage form for releasing a drug into an aqueous-fluid-containing environment in a plurality of sequential, pulsatile releasing events, said unit dosage form comprising:
   A) a tablet which disintegrates in an aqueous environment of use;
   B) a plurality of populations of pellets or particles enclosed within said tablet each population of pellets constructed to release a drug into said environment of use by bursting at a different particular release time interval after initial contact with said environment of use, whereby all of said pellets are released from said tablet substantially simultaneously and exposed to said environment of use substantially simultaneously when said tablet disintegrates;
   C) each pellet containing a core including said drug and a swelling agent other than said drug, said swelling agent having the property of increasing in volume on exposure to water; and
   D) a frangible, water-permeable membrane completely enclosing said core and preventing release of said drug into said environment of use, said membrane comprising at least one water-insoluble film forming polymer and at least one of:
      a) a water-soluble film forming polymer means which gradually dissolves and causes said membrane to become increasingly frangible as time in contact with water increases; and
      b) a permeability-reducing means which reduces the rate at which water passes through the membrane and thereby the rate of increase in volume of the swelling agent in the core, whereby the increasing volume of said swelling agent applies increasing internal force on said membrane and the rate at which said force is applied is determined by the water-permeability of said membrane, and the internal force at which said membrane will burst is determined by the frangibility of said membrane, and drug is released to said environment of use when the membrane enclosing said core bursts.

2. The unit dosage form according to claim 1, in which all of the populations have membranes with the same composition and the particular release time of a population is determined by the thickness of said membrane.

3. The unit dosage form according to claim 1, in which the particular release time of a population is determined at least in part by the relative proportions of said insoluble film forming polymer, said water-soluble film forming polymer means and said permeability reducing means in said membrane.

4. The unit dosage form according to claim 1, in which said water-soluble film forming polymer means has a greater solubility at alkaline pH.

5. The unit dosage form according to claim 1, in which said water-soluble film forming polymer means is substantially soluble at both alkaline, neutral and acid pH.

6. The unit dosage form according to claim 1, in which said swelling agent is selected from the group consisting of:
- cross-linked polyvinyl pyrrolidone;
- cross-linked carboxymethylcellulose;
- sodium starch glycolate and pregelatinized starch.

7. The unit dosage form according to claim 6, in which said water-insoluble film forming polymer is selected from the group consisting of: cellulose ester; acrylic resins; copolymers of acrylic acid and methacrylic acid esters with quaternary ammonium groups; and copolymers of acrylic acid and methacrylic acid esters.

8. The unit dosage form according to claim 7, in which said permeability-reducing means is selected from the group consisting of: fatty acids; waxes; and the salts of the fatty acids.

9. The unit dosage form according to claim 8, in which said water-soluble film forming polymer means is selected from the group consisting of: cellulose acetate phthalate; cellulose acetate trimellitate; hydroxypropyl methylcellulose phthalate; hydroxypropyl methylcellulose; polyvinyl pyrrolidone; shellac; and methacrylic acid copolymers.

10. The unit dosage form according to claim 1, in which said water-insoluble film forming polymer is selected from the group consisting of: cellulose ester; acrylic resins; copolymers of acrylic acid and methacrylic acid esters with quaternary ammonium groups; and copolymers of acrylic acid and methacrylic acid esters.

11. The unit dosage form according to claim 1, in which said permeability-reducing means is selected from the group consisting of: fatty acids; waxes; and the salts of the fatty acids.

12. The unit dosage form according to claim 1, in which said water-soluble film forming polymer means is selected from the group consisting of: cellulose acetate phthalate; cellulose acetate trimellitate; hydroxypropyl methylcellulose phthalate; hydroxypropyl methylcellulose; polyvinyl pyrrolidone; shellac; and methacrylic acid copolymers.

13. The unit dosage form according to claim 1, in which said water-insoluble film forming polymer comprises no less than half of the membrane.

14. A method for preparing a unit dosage form for releasing a drug into an aqueous fluid environment in a series of sequential, pulsatile releasing events, the method comprising the steps of:

A) preparing a plurality of pellets or particles comprising a drug and a swelling agent other than said drug;

B) completely enclosing each pellet or particle within a water-permeable frangible coating or membrane, the membrane arranged to admit water to said swelling agent and to burst when said swelling agent has expanded and thereby applied a particular force on said membrane;

C) composing said coating from a mixture comprising: water-permeable insoluble film forming polymer, water-permeable soluble film forming polymer; and a permeability reducing agent;

D) dividing said pellets into a plurality of populations of pellets in which each population is provided with pellets having a coating arranged to cause said pellets to burst open and release the drug at a particular burst time interval after becoming exposed to said aqueous fluid environment, and providing each population with a coating having a different burst time interval to thereby provide said sequential, pulsatile releasing events;

E) mixing the plurality of populations of pellets in a predetermined proportion mixture; and F) forming an aggregate of said mixture into a tablet which disintegrates in an aqueous fluid environment and releases said pellets to exposure to said aqueous fluid environment substantially simultaneously, to thereby prepare a unit dose in which said water-permeable soluble film forming polymer gradually dissolves and causes said coating to become increasingly frangible as time in contact with the aqueous fluid environment increases and said permeability reducing agent decreases the rate at which water passes through the membrane and thereby the expanding of said swelling agent, and the relative amounts of said soluble film forming polymer and said permeability reducing agent in coatings of each population, and the thickness of the coating, determine said particular burst time interval.

15. The method according to claim 14, in which the relative proportions of insoluble film forming polymer, soluble film forming polymer and permeability reducing agent are held constant in the coatings of all said populations and different burst time intervals are achieved by varying coating thickness.

16. The method according to claim 14, in which different burst time intervals are arranged by varying the relative proportions of said soluble film forming polymer, said insoluble film forming polymer, and said permeability reducing agent.

* * * * *